(12) United States Patent
Pezzotti et al.

(10) Patent No.: US 12,718,943 B2
(45) Date of Patent: Aug. 25, 2026

(54) FACILITATING INTERPRETABILITY OF CLASSIFICATION MODEL

(71) Applicant: KONINKLIJKE PHILIPS N.V., Eindhoven (NL)

(72) Inventors: Nicola Pezzotti, Eindhoven (NL); Jacek Lukasz Kustra, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1059 days.

(21) Appl. No.: 17/637,831

(22) PCT Filed: Aug. 31, 2020

(86) PCT No.: PCT/EP2020/074171
§ 371 (c)(1),
(2) Date: Feb. 24, 2022

(87) PCT Pub. No.: WO2021/038096
PCT Pub. Date: Mar. 4, 2021

(65) Prior Publication Data

US 2022/0285024 A1 Sep. 8, 2022

(30) Foreign Application Priority Data

Aug. 29, 2019 (EP) .................................... 19194471

(51) Int. Cl.
*G16H 50/20* (2018.01)
*G16H 10/60* (2018.01)

(52) U.S. Cl.
CPC ............. *G16H 50/20* (2018.01); *G16H 10/60* (2018.01)

(58) Field of Classification Search
CPC ..................................................... G16H 50/20
USPC ........................................................... 706/45
See application file for complete search history.

(56) References Cited

U.S. PATENT DOCUMENTS

2008/0058613 A1* 3/2008 Lang ..................... G06T 7/0012 600/300
2012/0189176 A1 7/2012 Giger
2012/0194646 A1* 8/2012 Chiang ................ G02B 21/008 348/46

(Continued)

FOREIGN PATENT DOCUMENTS

| JP | 2013206085 A | 10/2013 |
|---|---|---|
| WO | WO2009103156 A1 | 8/2009 |
| WO | WO2019032858 A1 | 2/2019 |

OTHER PUBLICATIONS

Hongsen et al., “Uncertainty-oriented Multidimensional Data Visual Analysis”, “CNKI dissertation”, vol. 2019, No. 02, Jun. 2017, pp. 1-66.

(Continued)

*Primary Examiner* — Austin Hicks

(57) ABSTRACT

A system and computer-implemented method are provided for generating a visualization of the classification uncertainty of a classification model which is applied to clinical data, wherein said visualization is provided in a lower-dimensional space which is obtained by applying a non-linear and manifold preserving dimensionality reduction technique to feature vectors of the clinical data. The visualization techniques consider the classification model as a ‘black box’ by not being dependent on internal parameters of the classification model.

20 Claims, 4 Drawing Sheets

(56) References Cited

U.S. PATENT DOCUMENTS

| | | | | |
|---|---|---|---|---|
| 2013/0096941 | A1* | 4/2013 | Kanada | G16H 50/70 705/2 |
| 2013/0135307 | A1* | 5/2013 | Kawasaki | G06T 15/08 345/424 |
| 2019/0034766 | A1 | 1/2019 | Chen | |
| 2019/0050474 | A1* | 2/2019 | Allen | G06N 20/00 |

OTHER PUBLICATIONS

Chen et al., "Study on Uncertainty Visualization and Analysis Method" "CNKI dissertation", vol. 2016, No. 01, Jan. 12, 2015.
PCT International Search Report, International application No. PCT/EP2020/074171, Nov. 11, 2020.
Höllt T. et al., "Cytosplore: Interactive Immune Cell Phenotyping for Large Single-Cell Datasets", Computer Graphics Forum, vol. 35, No. 3, Jun. 6, 2016 (Jun. 6, 2016), pp. 171-180, XP055671334.
Pezzotti N. et al., "Dimensionality-Reduction Algorithms for Progressive Visual Analytics", ASCI dissertation series, Apr. 8, 2019 (Apr. 8, 2019), XP055745921.
Höllt T. et al., "Cytosplore: Interactive Visual Single-Cell Profiling of the Immune System", EUROGRAPHICS 2019, May 10, 2019 (May 10, 2019), XP055745925.
Pezzotti N. et al., "Approximated and User Steerable tSNE for Progressive Visual Analytics", IEEE Transactions on Visualization and Computer Graphics, vol. 23, No. 7, pp. 1739-1752, Jul. 1, 2017.
Van Der Maaten L. et al., "Visualizing Data using t-SNE", Journal of Machine Learning Research, vol. 9, No. Nov, pp. 2579-2605, 2008.
Faust K. et al., "Visualizing Histopathologic Deep Learning Classification and Anomaly Detection Using Nonlinear Feature Space Dimensionality Reduction", BMC Bioinformatics, vol. 19, No. 173, pp. 1-15, 2018.
Chen Y. et al. "Machine Learning Techniques in Cancer Prognostic Modeling and Performance Assessment", Frontiers of Biostatistical Methods and Applications in Clinical Oncology, S. Matsui and J. Crowley, Eds. Singapore: Springer Singapore, 2017, pp. 193-230.
Friedman N. et al., "Bayesian Network Classifiers", Machine Learning, vol. 29, No. 2-3, pp. 131-163, 1997.
Sacha D. et al., "VIS4ML: An Ontology for Visual Analytics Assisted Machine Learning", IEEE Transactions on Visual Computer Graphics, Aug. 2018.
Hastie T. et al. "Unsupervised Learning," The Elements of Statistical Learning: Data Mining, Inference, and Prediction, Springer New York, 2009, pp. 485-585.
LeCun Y. et al., "Deep Learning", Nature, vol. 521, No. 7553, pp. 436-444, May 2015.
Raidou R. G. et al., "Visual Analytics for the Exploration of Tumor Tissue Characterization", Computer Graphics Forum, vol. 34, No. 3, pp. 11-20, 2015.
Van Der Maaten L. et al., "Accelerating t-SNE Using Tree-Based Algorithms", Journal of Machine Learning, vol. 15, No. 1, pp. 3221-3245, Jan. 2014.
Pezzotti N. et al., "Linear tSNE Optimization for the Web", May 2018.
Bentley J. L. et al., "Multidimensional Binary Search Trees Used for Associative Searching", Communications of the ACM, vol. 18, No. 9, pp. 509-517, Sep. 1975.
Cortes C. et al., "Support-Vector Networks", Machine Learning, vol. 20, No. 3, pp. 273-297, Sep. 1995.
Ho T. K. et al., "The Random Subspace Method for Constructing Decision Forests", IEEE Transactions on Pattern Analysis and Machine Intelligence, vol. 20, No. 8, pp. 832-844, Aug. 1998.
Bengio Y. et al., "Representation Learning: A Review and New Perspectives", IEEE Transactions on Pattern Analysis and Machine Intelligence, vol. 35, No. 8, pp. 1798-1828, Aug. 2013.

* cited by examiner

FACILITATING INTERPRETABILITY OF CLASSIFICATION MODEL

CROSS REFERENCE TO RELATED APPLICATIONS

This application is a U.S. national phase application of International Application No. PCT/EP2020/074171 filed Aug. 31, 2020, which claims the benefit of EP Application Serial No. 19194471.9 filed Aug. 29, 2019 and is incorporated herein by reference.

FIELD OF THE INVENTION

The invention relates to a system, such as a clinical decision support system, which is configured to apply a classification model to clinical data, such as patient data, and to a computer-implemented method for applying a classification model to clinical data. The invention further relates to a computer-readable medium comprising instructions for causing a processor system to perform the method.

BACKGROUND OF THE INVENTION

Clinical decision support systems are increasingly used in clinical practice, for example when prioritizing emergency room episodes or when predicting a treatment outcome for a given patient. The input for such clinical decision support systems is typically clinical data, such as patient data. A clinical decision support system may be configured to infer clinically relevant information from the clinical data. For that purpose, the clinical decision support system may apply a classification model to the clinical data which may provide a classification of the clinical data and may thereby implement at least part of a clinical decision-making process. The classification model may in many cases be a machine-learned ('trained') classification model, such as a trained neural network, Support-Vector Machine (SVN) model, etc. Such types of clinical decision support systems are also referred to as being 'data-driven' as they are not fully defined by experts anymore.

In the design of such data-driven clinical decision support systems, it is a concern to provide the decision-making entity (e.g., the physician) with trust in the clinical decision support information provided by the classification model, for example by providing the physician with an understanding of how this clinical information is calculated to establish sufficient trust in the clinical information.

An additional challenge in data-driven clinical decision support systems is that new data may be added, e.g., by retraining the classification model, in which case the physician may wish to understand how this affects the classification model's performance, not only in terms of technical metrics, but also in terms of how the decision-making process of the classification model is affected by the new data. For example, while it is possible that the model accuracy remains stable, the new decision-making process after re-training with the new data may be misleading. A typical example may be the classic "Anscombe's Quartet", where all datasets show the same statistics, but in reality, the data distributions are clearly different.

The difficulties in bringing transparency to the decision-making process are related to the fact that a classification model often resembles an opaque black-box where the user is only able to obtain insights in the model's input, output and the technical characteristics of the model, such as the accuracy or recall or other metrics such as Receiver Operating Characteristic (ROC). However, typically no insights are provided into the model's internal decision-making process. This is typically due to the model's complexity and the multi-dimensional aspects, which are hard to interpret by humans. Different approaches have been proposed to overcome this, such as Bayesian networks, which provide a visual graph of the feature relationships, or data visualization approaches allowing the user to interpret the data in a human interpretable way. However, these techniques are typically specific to a type of classification model and cannot be generalized to different types of classification models. This severely limits the applicability of such techniques.

SUMMARY OF THE INVENTION

It may be desirable to be able to facilitate the interpretability of a classification model's decision-making process in a more model agnostic manner.

In accordance with a first aspect of the invention, a system is provided which is configured to apply a classification model to clinical data.

The system comprises:

a data interface for accessing:
- clinical data comprising data instances which are each representable as a feature vector in a multi-dimensional feature space;
- a classification model configured to be applied to the feature vector to provide a classification of the respective data instance;

a processor subsystem configured to:
- apply a non-linear and manifold-preserving dimensionality reduction technique to all or a subset of the feature vectors to obtain a plurality of clinical data points in a lower-dimensional space;
- create synthetic data points in the lower-dimensional space and determine feature vectors for the synthetic data points by applying an interpolation technique to the feature vectors of the clinical data points, thereby obtaining an interpolated feature vector for each of the synthetic clinical data points;
- for each synthetic clinical data point:
- apply the classification model to the respective interpolated feature vector to obtain a classification for the synthetic clinical data point, and
- determine a classification uncertainty of the classification; and
- generate a visualization of the lower-dimensional space for display to a user, wherein the visualization comprises a visualization of the classification uncertainty in visual relation to the synthetic clinical data points.

In accordance with a further aspect of the invention, a computer-implemented method is provided for applying a classification model to clinical data.

The method comprises:

accessing:
- clinical data comprising data instances which are each representable as a feature vector in a multi-dimensional feature space;
- a classification model configured to be applied to the feature vector to provide a classification of the respective data instance;

applying a non-linear and manifold-preserving dimensionality reduction technique to all or a subset of the feature vectors to obtain a plurality of clinical data points in a lower-dimensional space;

creating synthetic data points in the lower-dimensional space and determining feature vectors for the synthetic data points by applying an interpolation technique to the feature vectors of the clinical data points, thereby obtaining an interpolated feature vector for each of the synthetic clinical data points;

for each synthetic clinical data point:

applying the classification model to the respective interpolated feature vector to obtain a classification for the synthetic clinical data point, and determining a classification uncertainty of the classification; and generating a visualization of the lower-dimensional space for display to a user, wherein the visualization comprises a visualization of the classification uncertainty in visual relation to the synthetic clinical data points.

In accordance with a further aspect of the invention, a computer-readable medium is provided comprising transitory or non-transitory data representing a computer program, the computer program comprising instructions for causing a processor system to perform the computer-implemented method.

The above measures involve accessing clinical data which may comprise several data instances which are each representable as a feature vector in a multi-dimensional feature space. For example, such clinical data may be patient data, and each data instance may relate to a different patient. In this example, the clinical data of a particular patient may form a feature vector in the multi-dimensional feature space. For example, if a particular data instance contains 33 values, such as sex, weight, height, blood type, etc., the data instance may be representable as a data point in a 33-dimensional feature space, with the coordinates of the data point representing the feature's values, e.g., 'F', '60 kg', '170 cm', 'O-negative', etc. Such representation of data as feature vectors is known per se in data classification.

Furthermore, a classification model may be accessed, e.g., in the form of a data representation of the classification model, e.g., as classification model data. The classification model, which may be a machine-learned classification model such as a neural network, SVN or the like, may be configured to be applied to the feature vector to provide a classification of the respective data instance. Such a classification may in general be an inference, e.g., a prediction, for example of a clinical diagnosis, and may in the context of clinical decision support constitute clinical decision support information which may support a user's decision-making.

The above measures further involve applying a non-linear and manifold-preserving dimensionality reduction technique to all or a subset of the feature vectors to obtain a plurality of clinical data points in a lower-dimensional space. Such non-linear and manifold-preserving dimensionality reduction techniques are known per se, and are based on the manifold assumption that states that (high-dimensional) data typically lies at least roughly on a low-dimensional manifold, with this being also the underlying assumption in various machine learning based techniques. A non-limiting example of such a non-linear and manifold-preserving dimensionality reduction technique is the t-distributed Stochastic Neighbor Embedding (t-SNE) algorithm. As a result of applying this technique, respective clinical data points are obtained in the lower-dimensional space. Here, 'lower-dimensional' refers to a dimensionality which is lower, and in some cases much lower, than the dimensionality of the original multi-dimensional feature space. In some examples, the dimensionality reducing technique may be a non-linear or manifold-preserving dimensionality reduction technique. Other examples of suitable techniques include but are not limited to UMAP, ISOMAP, HSNE and A-tSNE, each being known per se in the art of dimensionality reduction of multi-dimensional data.

As a result of the above, the lower-dimensional space, which may also be referred to as an 'embedding space', may now contain clinical data points which each have an associated higher-dimensional feature vector. Feature vectors for other data points in the lower-dimensional space may be obtained by applying an interpolation technique to the feature vectors of the clinical data points. For example, such an interpolation technique may involve applying a weighted average to the feature vectors of clinical data points in a neighborhood of the 'other' data point, in which the weighting is inversely proportionate to the distance to the respective clinical data points in the lower-dimensional space.

As a result, synthetic clinical data points may be obtained in the lower-dimensional space, referring to coordinates in the lower-dimensional space for which an interpolated feature vector has been determined in the above-described manner. For each of these synthetic clinical data points, a classification may be obtained by applying the classification model to the respective interpolated feature vector, and a classification uncertainty of the classification may be determined. Such a classification uncertainty may be determined in various known ways, and may in general depend on the type of classification model, as also elucidated elsewhere.

The above measures are based on the insight that the non-linear and manifold-preserving dimensionality reduction technique allows the feature space to be represented in a lower-dimensional manner in which the variance in the clinical data is preserved to at least a substantial degree. Such a lower-dimensional space is much easier to interpret for a human observer than the higher-dimensional feature space. For example, if the classification of the clinical data is plotted in such a lower-dimensional space, e.g., as a different visual representation overlaying each clinical data point, a user may more easily see decision boundaries in the classification by the classification model than in the original higher-dimensional feature space.

However, the clinical data which has been used as input to the dimensionality reduction technique may yield clinical data points which are distributed non-uniformly and/or sparsely across the lower-dimensional space.

It may be of interest to obtain visual feedback on the performance of the classification model also in other areas of the lower-dimensional space, e.g., in areas which do not contain any or a sufficient number of original clinical data points, as the classification model may later be applied to clinical data of which the corresponding clinical data points lie in such areas of the lower-dimensional space. This is addressed by generating the aforementioned synthetic clinical data points, which may for example be determined in a regular grid in the lower-dimensional space and which in general provide more data points in the lower-dimensional space and thereby increase the density of data points in the lower-dimensional space. Such increased density may greatly improve the interpretability of the visual feedback, particularly if the original clinical data points are only sparsely distributed.

The lower-dimensional space may then be visualized, e.g., as a 2D or 3D image in case of a 2D or 3D space, and the classification uncertainty associated with the interpolated feature vectors of the synthetic clinical data points may be visualized in visual relation to the synthetic data points. For example, the pixels or voxels representing the synthetic data points may be assigned a saturation or an intensity which represents the uncertainty. In some embodiments, the classification uncertainty of all clinical data points, i.e., original and synthetic, may be visualized.

Advantageously, the classification uncertainty across the lower-dimensional space may be shown to the user, which may indicate areas in which the uncertainty is particularly high (or the certainty particularly low). This may indicate a need for adjusting the classification model, e.g., by parameter tuning or otherwise, or if the classification model is a trained classification model, the need for more training data which comprises data instances in the particular area, or in general a need for the user to treat the classification by the classification model in this area cautiously.

Advantageously, the above measures provide a visualization of the classification uncertainty of a classification model across the lower-dimensional space while considering the classification model as a 'black box' by not being dependent on internal parameters of the classification model. Rather, the visualization is provided based on input (feature vectors) and output (classification) of the classification model and derived parameters (classification uncertainty). Advantageously, the above measures may facilitate the interpretability of a classification model's decision-making process in a more model agnostic manner.

Optionally, the processor subsystem is further configured to generate, in the visualization of the lower-dimensional space, a visualization of the classification by the classification model. In addition to the classification uncertainty, also the classification itself may be visualized. For example, the pixels or voxels in the 2D or 3D image may be assigned a saturation or an intensity which represents the classification uncertainty and a hue which represents the classification. This may enable a user to perceive classification boundaries, which may elsewhere also be referred to as 'decision boundaries', and in particular to perceive complex classifications boundaries which may indicate a poor generalization of the classification model to such areas.

Optionally, the system comprises a user interface subsystem comprising a display output for displaying said visualizations and a user input interface for receiving user input data from a user input device operable by a user, and the processor subsystem is configured to, via the user interface subsystem, enable a user to select a synthetic clinical data point, and in response to said selection, provide a visualization of the respective interpolated feature vector. This user interface functionality may enable a user to easily see the interpolated feature vector of a selected synthetic clinical data point, e.g., as a visualization of each feature vector component, which may in turn enable a user to draw conclusions on the relation between i) the classification and/or classification certainty and ii) the feature(s) on which the classification is based.

Optionally, the processor subsystem is configured to, via the user interface subsystem, enable the user to select two synthetic clinical data points, and in response to said selection, provide a visualization of a difference between the respective interpolated feature vectors. This user interface functionality may enable a user to easily see the differences in interpolated feature vectors between selected synthetic clinical data points, which may be particularly useful near classification boundaries, allowing a user to draw conclusions on the relation between a change in classification and the feature vector differences.

Optionally, the classification model is trained on training data, and the clinical data for which the visualization is provided is the training data of the classification model. The above measures may be applied to the training data itself, which may allow a user to obtain feedback on the classification and classification certainty with respect to the training data. This may for example indicate a need for more and/or a different type of training data.

Optionally, all or a subset of the data instance of the training data comprise or are associated with a respective ground truth classification, and the processor subsystem is configured to generate a visualization of the ground truth classification in visual relation with the clinical data points in the visualization of the lower-dimensional space. By visualizing the ground truth, a difference between the ground truth and the classification by the classification model may be made visible, which may indicate misclassifications or other problems.

Optionally, the data interface is configured to access further clinical data, and the processor subsystem is configured to:

generate further clinical data points representing the further clinical data in the lower-dimensional space; and visualize the further clinical data points in the visualization of the lower-dimensional space.

Such further clinical data point(s) may represent new input data after the training. By plotting such further clinical data point(s) in the lower-dimensional space, the spatial relation between the further clinical data point(s) and the original clinical data points may be made visible. For example, if both types of data points form separate clusters in the lower-dimensional space, this may, in case of a trained classification model, indicate that the classification model may be insufficiently generalized to classify the new input data. Furthermore, such visualization may allow a user to visually relate the new input data to the classification and classification certainty of the classification model.

Optionally, the processor subsystem is configured to determine the classification and the classification uncertainty, and to visualize the classification uncertainty, for a regular grid of synthetic clinical data points in the lower-dimensional space. The interpolated feature vectors, and in turn the classification and classification uncertainty relating to said interpolated feature vectors, may be determined for data points in a regular grid. For example, if the lower-dimensional space is visualized as a 2D image, the classification and classification uncertainty may be determined for each pixel of the 2D image.

Optionally, the non-linear and manifold-preserving dimensionality reduction technique is a t-distributed Stochastic Neighbor Embedding (t-SNE) algorithm. Alternative algorithms include, but are not limited to UMAP, ISOMAP, HSNE and A-tSNE. Optionally, applying the interpolation technique comprises using a KD-tree algorithm to search for clinical data points to be used in the interpolation. The KD-tree algorithm may be used to find a set of K-Nearest Neighbor (KNN) clinical data points for interpolation. Alternatively, any other algorithm may be used for KNN computation. Examples of such algorithms include but are not limited to approximate KD-Trees and hashing techniques.

Optionally, the system is part of a workstation or imaging apparatus.

It will be appreciated by those skilled in the art that two or more of the above-mentioned embodiments, implementations, and/or optional aspects of the invention may be combined in any way deemed useful.

Modifications and variations of a system, computer-implemented method and/or any computer program product, which correspond to the described modifications and variations of another one of said entities, can be carried out by a person skilled in the art on the basis of the present description.

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the figures, elements which correspond to elements already described may have the same reference numerals.

LIST OF REFERENCE NUMBERS

Figure 2:
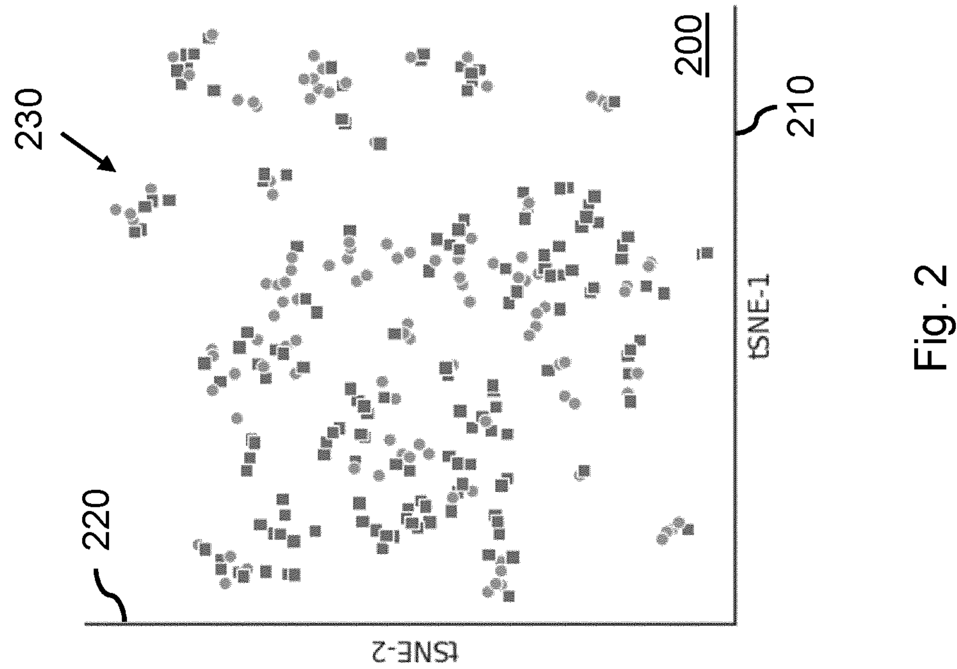
FIG. 2 illustrates a result of a dimensionality reduction applied to data instances which are representable as feature vectors in a 33-dimensional feature space, obtaining clinical data points in a two-dimensional space.

The following list of reference numbers is provided for facilitating the interpretation of the drawings and shall not be construed as limiting the claims.

20 data storage
30 clinical data
40 model data
50 visualization data
60 user input device
62 user input data
80 display
100 system for applying classification model to clinical data
120 data interface
122 external data communication
124 internal data communication
140 processor subsystem
142 internal data communication
160 user interface subsystem
170 user input interface
180 display output
182 display data
200 lower-dimensional space
210 t-SNE-1 dimension
220 t-SNE-2 dimension
230 clinical data point with ground-truth classification
300 visualization of classification and classification uncertainty of synthetic clinical data points as 2D image
310, 312 complex decision boundaries in classification
320 misclassification in ground-truth
330 areas with low classification confidence
340 areas with high classification confidence
350 selection of synthetic clinical data point
360 selection of two synthetic clinical data points
400 visualization of interpolated feature vector
410 visualization of difference in interpolated feature vectors
420 feature value axis
422 feature value difference axis
430 feature component axis
500 method of applying classification model to clinical data
510 accessing clinical data
520 accessing classification model
530 applying dimensionality reduction technique
540 determining feature vectors for other data points
550 determining classification and classification uncertainty
560 generating visualization of classification uncertainty
600 computer-readable medium
610 non-transitory data

DETAILED DESCRIPTION OF EMBODIMENTS

Figure 1:
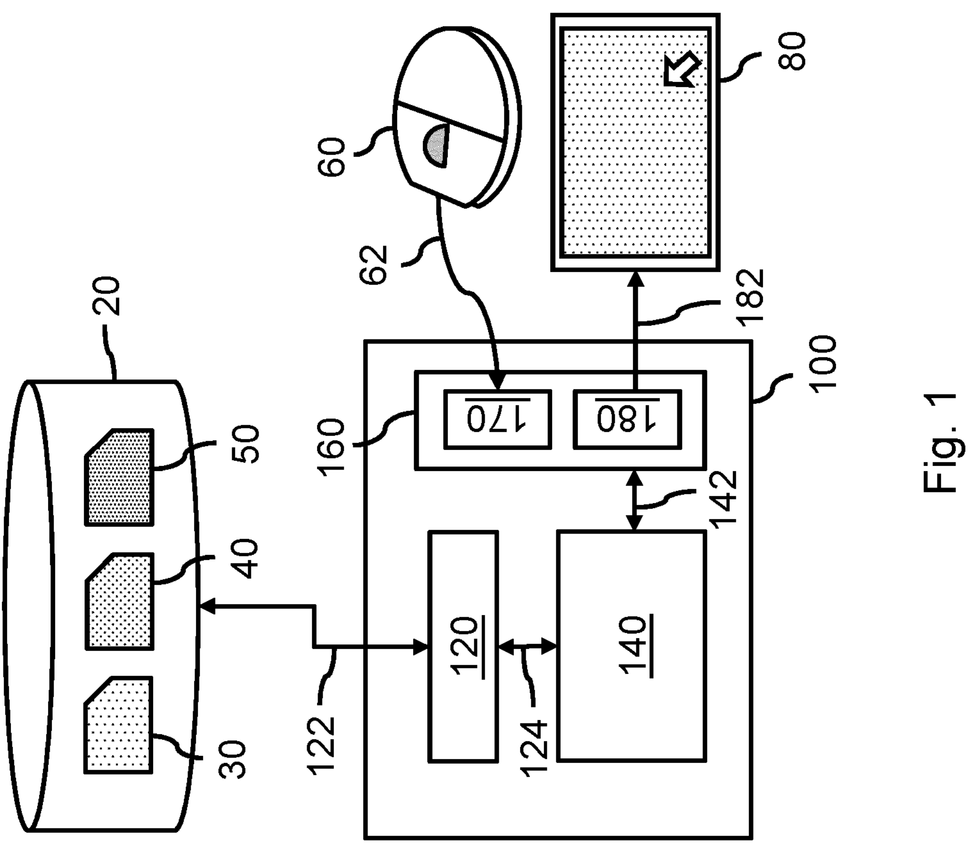
FIG. 1 shows a system for applying a classification model to clinical data and which is configured to generate a visualization of a classification uncertainty of the classification model and to display said visualization.

FIG. 1 shows a system 100 for applying a classification model to clinical data and which may be configured to generate a visualization of a classification uncertainty of the classification model and to display said visualization.

The system 100 is shown to comprise a data interface 120 for accessing clinical data 30 comprising data instances which are each representable as a feature vector in a multi-dimensional feature space. For example, the clinical data 30 may comprise data records for a plurality of patients, with each data record representing a data instance. For example, as also shown in FIG. 1, the data interface 120 may provide data access 122 to an external data storage 20 which may comprise said clinical data 30. The data storage 20 may, for example be constituted by, or be part of, a Picture Archiving and Communication System (PACS) or an Electronic Medical Record (EMR) database of a Hospital Information System (HIS) to which the system 100 may be connected or comprised in. Alternatively, the data interface 120 may provide data access to an internal data storage which is part of the system 100. Alternatively, the clinical data 30 may be accessed via a network. In general, the data interface 120 may take various forms, such as a network interface to a local or wide area network, e.g., the Internet, a storage interface to an internal or external data storage, etc. The data storage 20 may take any known form, such as a hard drive or an array of hard drives or an SSD or an array of SSDs.

The data storage 20 is further shown to comprise model data 40 defining a classification model for being applied to the feature vector to provide a classification of the respective data instance. Depending on the embodiment, the data storage 20 may comprise one or both types of data 30, 40. In some embodiments, the clinical data 30 and the model data 40 may each be accessed from a different data storage, e.g., via a different subsystem of data interface 120. Each subsystem may be of a type as described above for the data interface 120.

The system 100 is further shown to comprise a processor subsystem 140 which may internally communicate with the data interface 120 via data communication 124. The processor subsystem 140 may be configured to, during the operation of the system 100, apply a non-linear and manifold-preserving dimensionality reduction technique to all or a subset of the feature vectors to obtain a plurality of clinical data points in a lower-dimensional space, determine feature vectors for other data points in the lower-dimensional space by applying an interpolation technique to the feature vectors of the clinical data points, thereby obtaining synthetic clinical data points in the lower-dimensional space each having an interpolated feature vector, and for each synthetic clinical data point, apply the classification model to the respective interpolated feature vector to obtain a classification for the synthetic clinical data point, and determine a classification uncertainty of the classification. The processor subsystem 140 may be further configured to generate a visualization of the lower-dimensional space for display to a user, wherein the visualization comprises a visualization of the classification uncertainty in visual relation to the synthetic clinical data points. Such visualization may be stored in the data storage 20, e.g., in the form of visualization data 50.

It is noted that the operation of the system 100, including various optional aspects thereof, will be further explained with reference to FIGS. 2-4C.

As an optional component, the system 100 is shown to comprise a user interface subsystem 160. The processor subsystem 140 may communicate with the user interface subsystem 160 via internal data communication 142. The user interface subsystem 160 may be configured to, during operation of the system 100, enable a user to interact with the system 100, for example using a graphical user interface. The user interface subsystem 160 is shown to comprise a user input interface 170 configured to receive user input data 62 from a user input device 60 operable by the user. The user input device 60 may take various forms, including but not limited to a computer mouse, touch screen, keyboard, microphone, etc. FIG. 1 shows the user input device to be a computer mouse 60. In general, the user input interface 170 may be of a type which corresponds to the type of user input device 60, i.e., it may be a thereto corresponding type of user device interface 60. The user interface subsystem 160 is further shown to comprise a display output 180 configured to provide display data 182 to a display 80 to visualize output of the system 100, such as the aforementioned visualization of the lower-dimensional space and other types of visualizations. In the example of FIG. 1, the display is an external display 80. Alternatively, the display may be an internal display.

In general, the system 100 may be embodied as, or in, a single device or apparatus, such as a workstation, e.g., laptop or desktop-based, or a server. The device or apparatus may comprise one or more microprocessors which execute appropriate software. For example, the processor subsystem may be embodied by a single Central Processing Unit (CPU), but also by a combination or system of such CPUs and/or other types of processing units. The software may have been downloaded and/or stored in a corresponding memory, e.g., a volatile memory such as RAM or a non-volatile memory such as Flash. Alternatively, the functional units of the system, e.g., the data interface and the processor subsystem, may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses, such as distributed servers, e.g., in the form of cloud computing.

FIG. 2 illustrates a result of a dimensionality reduction applied to clinical data. In this example, the clinical data comprises individual data instances, for example representing data of respective patients or exams, which are each representable as a feature vector in a 33-dimensional feature space. A manifold is assumed to exist in the 33-dimensional feature space which sufficiently represents the clinical data. In other words, it is assumed that feature redundancy exists and that the variance in the clinical data is on a lower-dimensional structure embedded in the high-dimensional space. The data on such a lower-dimensional structure may be represented in a lower-dimensional space, such as a 2D space, using a non-linear and manifold preserving dimensionality reduction technique (also simply referred to as a non-linear projection technique), for example using a so-called t-SNE algorithm.

The result of applying such a t-SNE algorithm to the clinical data is shown in FIG. 2, in which a visualization of the lower-dimensional space 200 is shown having two dimensions 210, 220 labelled tSNE-1 and tSNE-2. In addition, clinical data points 230 are shown which represent the higher-dimensional feature vectors of the clinical data in the lower-dimensional space. The dimensionality reduction may be such that clinical data points 230 which are nearby to each other in the 2D space 200 have similar feature vectors. It will be appreciated that many alternatives exist to t-SNE, such as UMAP, ISOMAP, HSNE and A-tSNE, all of which are known per se. In case t-SNE is used as a dimensionality reduction algorithm, the so-called approximated-tSNE implementation of tSNE may be used for desktop applications or TensorFlow.js tSNE for web applications.

In the example of FIGS. 2-4C, the clinical data is the training data which has been used for training the classification model. Such training data may be labelled, in that there exists a ground truth for the classification by the classification model. As shown in FIGS. 2-4C, this labelling may be visualized, e.g., by distinguishing between two categories as either a darker square or a lighter circle.

Figure 3B:
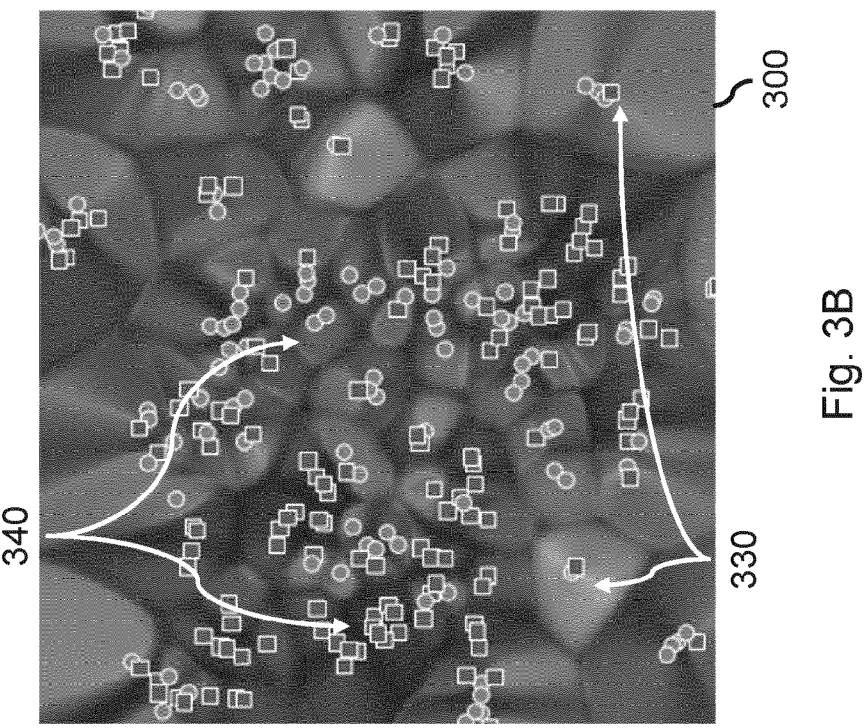
FIG. 3B shows the visualization of FIG. 3A, and shows areas where the classification model has low confidence and where it has high confidence.
Figure 3A:
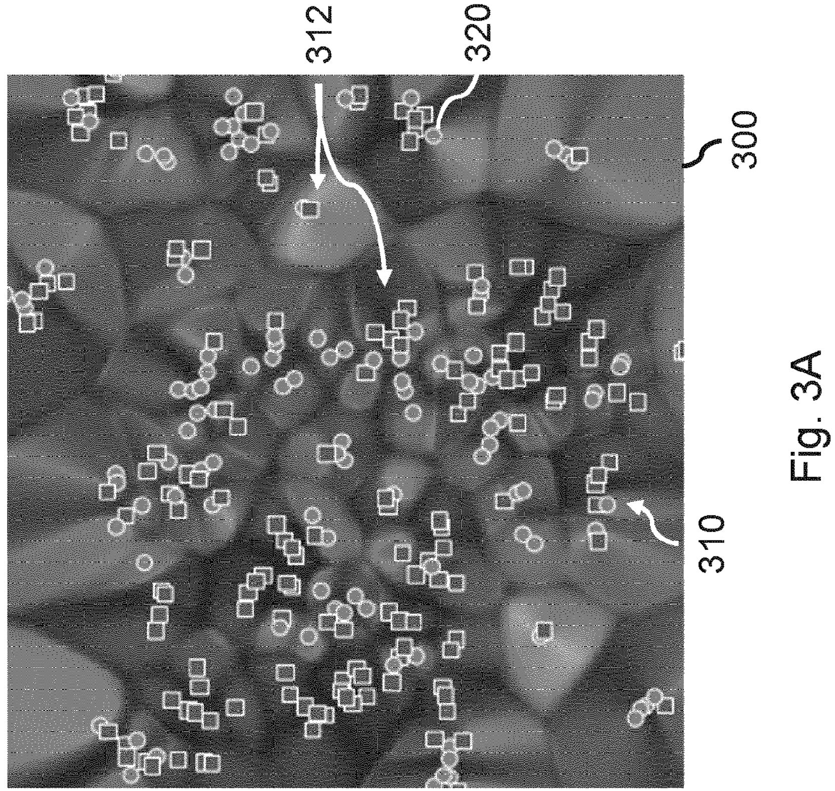
FIG. 3A shows a visualization of the classification and the classification uncertainty of the classification model in the two-dimensional space, illustrating several complex decision boundaries in the two-dimensional space.

FIG. 3A shows a visualization 300 of the classification and the classification uncertainty of the classification model in the two-dimensional space. Such a visualization 300 may have been generated by the system 100 of FIG. 1 by, for a dense and regular grid of synthetic clinical data points in the two-dimensional space of FIG. 2, applying the classification model to the interpolated feature vector associated with a respective synthetic clinical data point to obtain a classification, and by determining the classification uncertainty. In determining the interpolated feature vectors, the so-called KD-Tree algorithm may be used to search for nearest datapoints to be used in the interpolation. The interpolation itself may be any suitable weighted or non-weighted interpolation technique which is applied to the set of datapoints which is found using the KD-Tree algorithm, e.g., the KNN datapoints.

This visualization 300 may be termed a 'classification landscape', and may be generated in an output-driven manner, in that the dense and regular grid of synthetic clinical data points may correspond to the pixel grid of the output image containing the visualization. Alternatively, any other suitable regular grid may be used, or an irregular grid or any other set of synthetic clinical data points.

As is also shown in the examples of FIGS. 3A-4A, the classification may be visualized by selecting a hue for a respective pixel, while the classification uncertainty may be visualized by selecting a color saturation for the respective pixel. For example, areas of high confidence (or high certainty or low uncertainty) may be visualized with a high color saturation while areas of low confidence (or low certainty or high uncertainty) may be visualized with a low color saturation. It will be appreciated that alternatively, any other type of visualization may be used, as are known per se from the field of data visualization, including but not limited to using patterns instead of hue/saturation, using heat maps, using contour lines, etc.

It can be seen in FIG. 3A that there exist complex decision boundaries 310, 312 in the classification, in that the decision boundaries are very high-dimensional and poorly representable in lower-dimensional space, which may be apparent in the visualization in various ways, such as having decision boundaries in very close vicinity of each other. Such complex decision boundaries may indicate poor generalization of the classification model, and hence may require careful judgement by the clinician. From the visualization 300, the clinician may also detect possible misclassifications 320 as the ground truth classification may mismatch the classification by the classification model, the latter being represented in FIG. 3A by the underlying hue. Such misclassification may be a misclassification in the ground truth, e.g., in the form of an outlier, but may also be a misclassification by the classification model.

FIG. 3B shows the visualization 300 of FIG. 3A, and shows areas where the classification model has low confidence, being areas 330 which are visualized with a low color saturation, and where the classification model has high confidence, being areas 340 which are visualized with a high color saturation. In general, the classification uncertainty may also be referred to as classification certainty, referring to the complement of the classification uncertainty, or classification confidence or the like. Such classification (un) certainty may be determined in various ways. For example, for support-vector machines, the classification certainty may be determined as the distance from the decision boundary, while for random-forest classifiers, the classification certainty may correspond to the percentage of trees agreeing on the predictions, while for deep-learning based methods, the classification certainty may be derived from the entropy of the probability vector. Determining such a classification (un)certainty or confidence is known per se in data classification.

In general, the classification landscape 300 of FIGS. 3A and 3B may show a global behavior of the classification model. As indicated above, misclassified points 320 may be seen over the landscape, and the shape of the classification boundaries may be revealed. At the same time, the classification landscape 300 may be generated in a classification model agonistic manner, in that no internal parameters of the classification model may be needed to generate the classification landscape 300. In some embodiments, new clinical data may also be shown in the classification landscape, e.g., as new clinical data points obtained by the aforementioned dimensionality reduction. Depending on the location of the new clinical data points in the classification landscape 300, a clinician may determine whether the output of the classification model can be trusted or not.

In general, the classification landscape may be generated for any type of classification model, including but not limited to support-vector machines, decision trees, random forest classifier, or deep-learning based classification models.

Figures 4A, 4B, 4C:
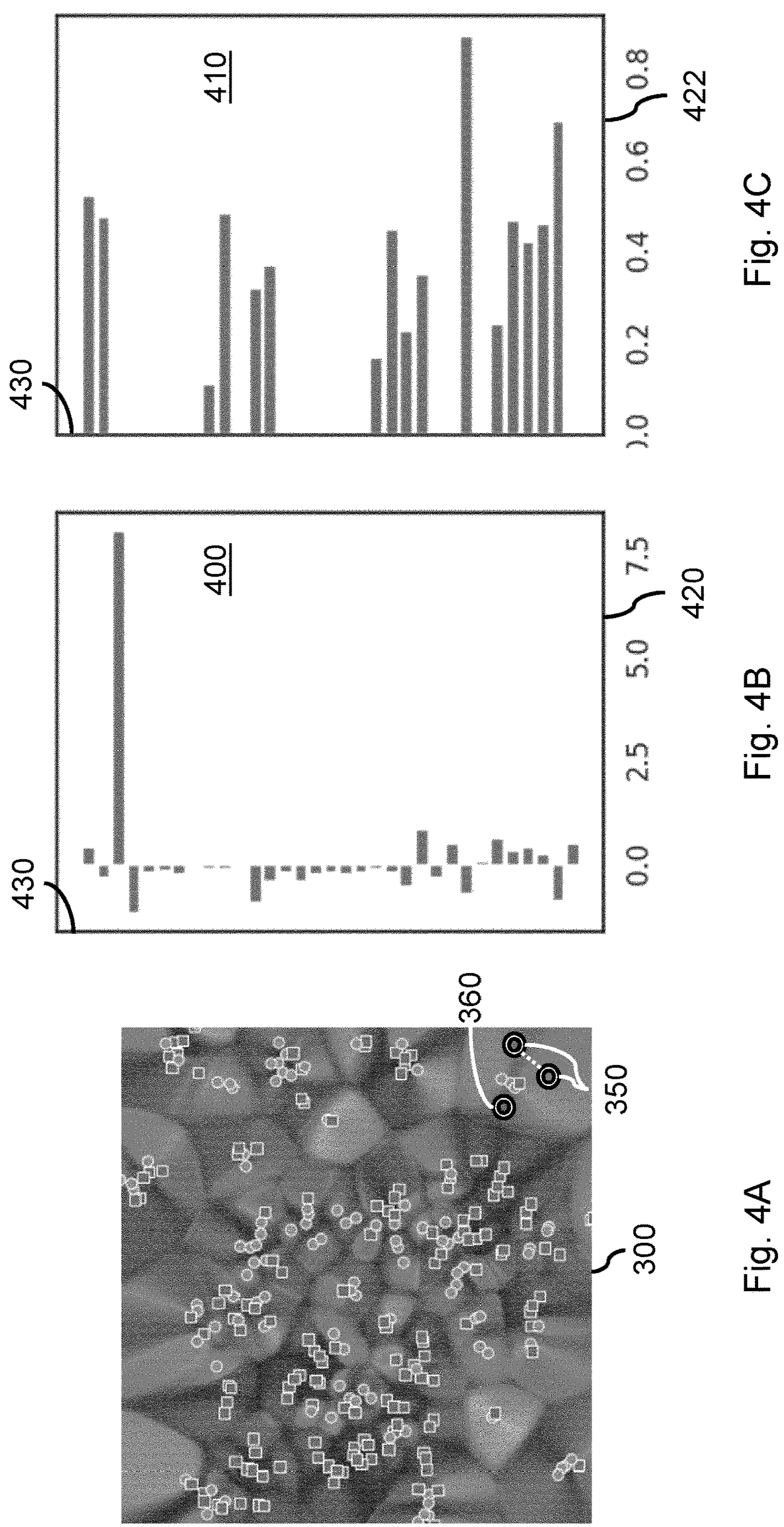
FIG. 4A illustrates a user selecting synthetic clinical data points in the visualization of the two-dimensional space.
FIG. 4B shows a visualization of an interpolated feature vector which may be provided in response to a selection of a synthetic clinical data point.
FIG. 4C shows a visualization of a difference between two interpolated feature vectors which may be provided in response to a selection of two synthetic clinical data points, for example at opposite sides of a decision boundary.

FIG. 4A illustrates a user selecting synthetic clinical data points in the visualization 300 of the two-dimensional space, for example using the user interface subsystem of the system 100 of FIG. 1 and a thereto connected mouse, touch screen or the like. Depending on whether a single synthetic clinical data point 360 or two of such data points 350 are selected, a different visualization may be generated.

FIG. 4B shows a visualization 400 of an interpolated feature vector which may be provided in response to a selection of the single synthetic clinical data point 360. Here, the vertical axis 430 may list the various feature vector components, such as for example sex, weight, height, blood type, etc., while the horizontal axis 420 may show the feature vector values, such as for example 'F', '60 kg', '170 cm', 'O-negative'. In this example, the feature vector is shown to comprise 33 features, e.g., from 0 to 32. Such a visualization 400 may enable a user to draw conclusions on the relation between on the one hand the classification and/or classification certainty and on the other hand the feature(s) on which the classification is based.

FIG. 4C shows a visualization 410 of a difference between two interpolated feature vectors which may be provided in response to the selection of the two synthetic clinical data points 350, being in this example at opposite sides of a decision boundary. Here, the vertical axis 430 may again list the various feature vector components, while the horizontal axis 422 may show the feature vector value differences. Such a visualization 410 may allow a user to draw conclusions on the relation between a change in classification and the feature vector differences.

Figure 5:
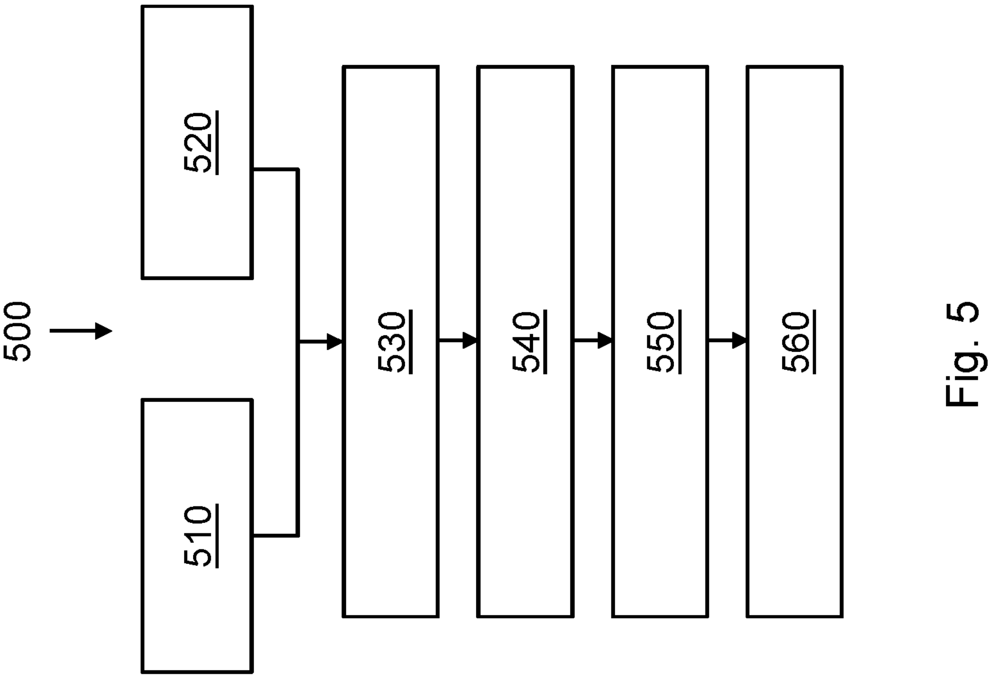
FIG. 5 shows a computer-implemented method for applying a classification model to clinical data and for generating a visualization of a classification uncertainty of the classification model for display to a user.

FIG. 5 shows a computer-implemented method 500 for applying a classification model to clinical data. The method 500 may correspond to an operation of the system 100 of FIG. 1. However, this is not a limitation, in that the method 500 may also be performed using another system, apparatus or device.

The method 500 is shown to comprise, in a step titled "ACCESSING CLINICAL DATA", accessing 510 clinical data comprising data instances which are each representable as a feature vector in a multi-dimensional feature space. The method 500 is further shown to comprise, in a step titled "ACCESSING CLASSIFICATION MODEL", accessing 520 a classification model configured to be applied to the feature vector to provide a classification of the respective data instance. The method 500 is further shown to comprise, in a step titled "APPLYING DIMENSIONALITY REDUCTION TECHNIQUE", applying 530 a non-linear and manifold-preserving dimensionality reduction technique to all or a subset of the feature vectors to obtain a plurality of clinical data points in a lower-dimensional space. The method 500 is further shown to comprise, in a step titled "DETERMINING FEATURE VECTORS FOR OTHER DATA POINTS", determining 540 feature vectors for other data points in the lower-dimensional space by applying an interpolation technique to the feature vectors of the clinical data points, thereby obtaining synthetic clinical data points in the lower-dimensional space each having an interpolated feature vector. The method 500 is further shown to comprise, in a step titled "DETERMINING CLASSIFICATION AND CLASSIFICATION UNCERTAINTY", for each synthetic clinical data point, applying 550 the classification model to the respective interpolated feature vector to obtain a classification for the synthetic clinical data point, and determining 550 a classification uncertainty of the classification. The method 500 is further shown to comprise, in a step titled "GENERATING VISUALIZATION OF CLASSIFICATION UNCERTAINTY", generating 560 a visualization of the lower-dimensional space for display to a user, wherein the visualization comprises a visualization of the classification uncertainty in visual relation to the synthetic clinical data points.

It will be appreciated that, in general, the operations of the computer-implemented method 500 of FIG. 5 may be performed in any suitable order, e.g., consecutively, simultaneously, or a combination thereof, subject to, where applicable, a particular order being necessitated, e.g., by input/output relations.

Figure 6:
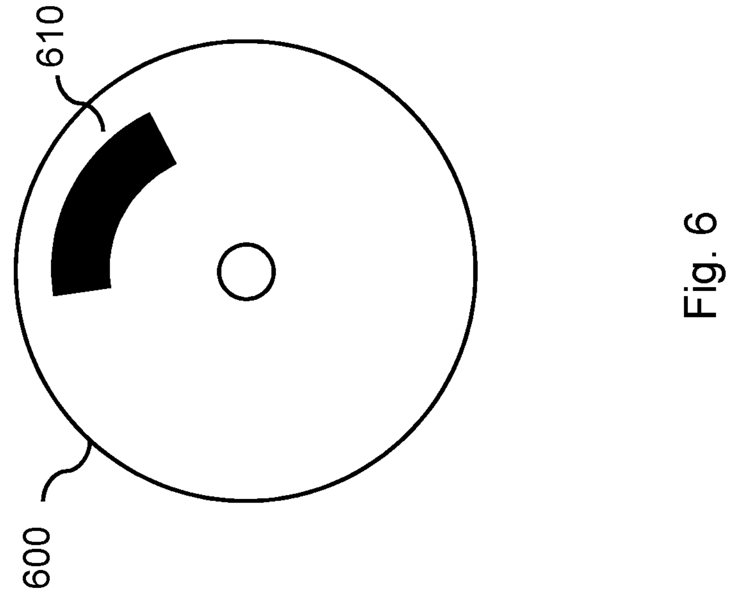
FIG. 6 shows a computer-readable medium comprising data.

The method(s) may be implemented on a computer as a computer implemented method, as dedicated hardware, or as a combination of both. As also illustrated in FIG. 6, instructions for the computer, e.g., executable code, may be stored on a computer readable medium 600, e.g., in the form of a series 610 of machine-readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 6 shows an optical disc 600.

Examples, embodiments or optional features, whether indicated as non-limiting or not, are not to be understood as limiting the invention as claimed.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. Expressions such as "at least one of" when preceding a list or group of elements represent a selection of all or of any subset of elements from the list or group. For example, the expression, "at least one of A, B, and C" should be understood as including only A, only B, only C, both A and B, both A and C, both B and C, or all of A, B, and C. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for visualizing classification uncertainty of a classification model, the system comprising:

a data interface configured to access:

clinical data comprising data instances which are each representable as a feature vector in a multi-dimensional feature space;

the classification model configured to be applied to the feature vector to provide a classification of the respective data instance; and a processor subsystem configured to:

apply a non-linear and manifold-preserving dimensionality reduction technique to all or a subset of the feature vectors to obtain a plurality of clinical data points in a lower-dimensional space wherein the lower-dimensional space is a two-dimensional space;

determine interpolated feature vectors in the multi-dimensional feature space by applying an interpolation technique to the feature vectors of the clinical data points;

create a plurality of synthetic clinical data points at coordinates in the lower-dimensional space corresponding to the determined interpolated feature vectors in the multi-dimensional feature space, wherein the lower-dimensional space is a lower dimension than the multi-dimensional feature space:

for each synthetic clinical data point:

apply the classification model to the respective interpolated feature vector to obtain a classification for the synthetic clinical data point, and determine the classification uncertainty of the classification; and generate a visualization of the lower-dimensional space for display to a user, wherein the visualization comprises a visualization of the classification uncertainty in visual relation to the synthetic clinical data points;

generate, in the visualization of the lower-dimensional space with the visualization of the classification uncertainty, a visualization of the classification by the classification model; and generate the visualization as a 2D image in which the classification uncertainty is assigned to a visual property of respective pixels of the 2D image.

2. The system according to claim 1, wherein the visual property is a saturation or an intensity of a respective pixel.

3. The system according to claim 2, further comprising a user interface subsystem comprising:

a display configured to display the visualizations; and a user input interface configured to receive user input data from a user input device operable by a user;

wherein the processor subsystem is further configured to, via the user interface subsystem, enable a user to select a synthetic clinical data point, and in response to the selection, provide a visualization of the respective interpolated feature vector.

4. The system according to claim 3, wherein the processor subsystem is further configured to, via the user interface subsystem, enable the user to select two synthetic clinical data points, and in response to the selection, provide a visualization of a difference between the respective interpolated feature vectors.

5. The system according to claim 1, wherein the classification model is trained on training data, and wherein the clinical data for which the visualization is provided is the training data of the classification model.

6. The system according to claim 5, wherein all or a subset of the data instance of the training data comprise or are associated with a respective ground truth classification, and wherein the processor subsystem is further configured to generate a visualization of the ground truth classification in visual relation with the clinical data points in the visualization of the lower-dimensional space.

7. The system according to claim 1, wherein the data interface is further configured to access further clinical data, and wherein the processor subsystem is further configured to:

generate further clinical data points representing the further clinical data in the lower-dimensional space; and visualize the further clinical data points in the visualization of the lower-dimensional space.

8. The system according to claim 1, wherein the processor subsystem is further configured to: determine the classification and the classification uncertainty, and visualize the classification uncertainty, for a regular grid of synthetic clinical data points in the lower-dimensional space.

9. The system according to claim 1, wherein the non-linear and manifold-preserving dimensionality reduction technique is a t-distributed Stochastic Neighbor Embedding (t-SNE) algorithm.

10. The system according to claim 1, wherein applying the interpolation technique comprises using a KD-tree algorithm to search for clinical data points to be used in the interpolation.

11. A workstation or imaging apparatus comprising the system according to claim 1.

12. A computer-implemented method for visualizing classification uncertainty of a classification model, the method comprising:

accessing:

clinical data comprising data instances which are each representable as a feature vector in a multi-dimensional feature space; and the classification model configured to be applied to the feature vector to provide a classification of the respective data instance;

applying a non-linear and manifold-preserving dimensionality reduction technique to all or a subset of the feature vectors to obtain a plurality of clinical data points in a lower-dimensional space, wherein the lower-dimensional space is a two-dimensional (2D) space;

determining interpolated feature vectors in the multi-dimensional feature space by applying an interpolation technique to the feature vectors of the clinical data points;

creating a plurality of synthetic clinical data points at coordinates in the lower-dimensional space corresponding to the determined interpolated feature vectors in the multi-dimensional feature space, wherein the lower-dimensional space is a lower dimension than the multi-dimensional feature space:

for each synthetic clinical data point:

applying the classification model to the respective interpolated feature vector to obtain a classification for the synthetic clinical data point, and determining the classification uncertainty of the classification; and generating a visualization of the lower-dimensional space for display to a user, wherein the visualization comprises a visualization of the classification uncertainty in visual relation to the synthetic clinical data points, wherein the visualization is generated as a 2D image in which the classification uncertainty is assigned to a visual property of respective pixels of the 2D image;

generating, in the visualization of the lower-dimensional space with the visualization of the classification uncertainty, a visualization of the classification by the classification model; and generating the visualization as a 2D image in which the classification uncertainty is assigned to a visual property of respective pixels of the 2D image.

13. A non-transitory computer-readable storage medium having stored instructions for visualizing classification uncertainty of a classification model, the instructions, when executed by a processor, cause the processor to:

access clinical data comprising data instances which are each representable as a feature vector in a multi-dimensional feature space;

access the classification model configured to be applied to the feature vector to provide a classification of the respective data instance;

apply a non-linear and manifold-preserving dimensionality reduction technique to all or a subset of the feature vectors to obtain a plurality of clinical data points in a lower-dimensional space wherein the lower-dimensional space is a two-dimensional space;

determine interpolated feature vectors in the multi-dimensional feature space by applying an interpolation technique to the feature vectors of the clinical data points;

create a plurality of synthetic clinical data points at coordinates in the lower-dimensional space corresponding to the determined interpolated feature vectors in the multi-dimensional feature space, wherein the lower-dimensional space is a lower dimension than the multi-dimensional feature space;

for each synthetic clinical data point:

apply the classification model to the respective interpolated feature vector to obtain a classification for the synthetic clinical data point, and determine the classification uncertainty of the classification, and generate a visualization of the lower-dimensional space for display to a user, wherein the visualization comprises a visualization of the classification uncertainty in visual relation to the synthetic clinical data points;

generate, in the visualization of the lower-dimensional space with the visualization of the classification uncertainty, a visualization of the classification by the classification model; and generate the visualization as a 2D image in which the classification uncertainty is assigned to a visual property of respective pixels of the 2D image.

14. The non-transitory computer-readable storage medium according to claim 13, wherein the visual property is a saturation or an intensity of a respective pixel.

15. The non-transitory computer-readable storage medium according to claim 13, wherein the instructions, when executed by the processor, further cause the processor to enable the user to select a synthetic clinical data point, and in response to the selection, provide a visualization of a difference between the respective interpolated feature vectors.

16. The non-transitory computer-readable storage medium according to claim 15, wherein the classification model is trained on training data and all or a subset of the data instance of the training data comprise or are associated with a respective ground truth classification, and wherein the instructions, when executed by the processor, further cause the processor to generate a visualization of the ground truth classification in visual relation with the clinical data points in the visualization of the lower-dimensional space.

17. The non-transitory computer-readable storage medium according to claim 13, wherein the instructions, when executed by the processor, further cause the processor to:

access further clinical data;

generate further clinical data points representing the further clinical data in the lower-dimensional space; and visualize the further clinical data points in the visualization of the lower-dimensional space.

18. The non-transitory computer-readable storage medium according to claim 13, wherein the instructions, when executed by the processor, further cause the processor to: determine the classification and the classification uncertainty, and visualize the classification uncertainty, for a regular grid of synthetic clinical data points in the lower-dimensional space.

19. The non-transitory computer-readable storage medium according to claim 13, wherein the non-linear and manifold-preserving dimensionality reduction technique is a t-distributed Stochastic Neighbor Embedding (t-SNE) algorithm.

20. The non-transitory computer-readable storage medium according to claim 13, wherein applying the interpolation technique comprises using a KD-tree algorithm to search for clinical data points to be used in the interpolation.

* * * * *